(12) United States Patent
Braun et al.

(10) Patent No.: US 7,932,339 B2
(45) Date of Patent: Apr. 26, 2011

(54) METHOD FOR PRODUCING WATER-SOLUBLE COMB-SHAPED COPOLYMERS

(75) Inventors: Olivier Braun, Castres (FR); Paul Mallo, Croissy sur Seine (FR); Jean-Louis Viovy, Paris Cedex (FR); Jérémie Weber, Paris Cedex (FR)

(73) Assignees: Centre National de la Recherche Scientifique, Paris (FR); Institut Curie, Paris (FR); Societe d'Exploitation de Produits pour les Industries Chimiques SEPPIC, Paris (FR)

( * ) Notice: Subject to any disclaimer, the term of this patent is extended or adjusted under 35 U.S.C. 154(b) by 700 days.

(21) Appl. No.: 11/921,000

(22) PCT Filed: May 18, 2006

(86) PCT No.: PCT/FR2006/050452
§ 371 (c)(1),
(2), (4) Date: Jan. 28, 2008

(87) PCT Pub. No.: WO2007/000535
PCT Pub. Date: Jan. 4, 2007

(65) Prior Publication Data
US 2010/0048839 A1      Feb. 25, 2010

(30) Foreign Application Priority Data

May 25, 2005  (FR) ...................................... 05 51369

(51) Int. Cl.
*C08F 20/00*      (2006.01)
(52) U.S. Cl. ................ 526/303.1; 526/307.1; 526/307.2

(58) Field of Classification Search ............... 525/303.1, 525/307.1, 307.2; 526/303.1, 307.1, 307.2
See application file for complete search history.

(56) References Cited

U.S. PATENT DOCUMENTS

| 5,885,432 A | 3/1999 | Hooper |
| 2004/0084310 A1 | 5/2004 | Viovy |
| 2004/0101970 A1 | 5/2004 | Viovy |

FOREIGN PATENT DOCUMENTS

WO      WO 00/40958      7/2000

*Primary Examiner* — Edward J Cain
(74) *Attorney, Agent, or Firm* — Young & Thompson

(57) ABSTRACT

Method for producing a comb-shaped copolymer whose skeleton is of an acrylamide, acrylic acid, acryloyl aminoethanol or dimethyl acrylamide type and on which poly(N-alkyl acrylamide) or poly(N,N-5 dialkyl acrylamide lateral segments are grafted, includes (a) producing a telomer poly(N-alkyl acrylamide) or poly(N,N-dialkyl acrylamide) of formula (I) $H_2N-R_1-Z-\{CH_2-C(R_2)[C(=O)N(R_3)(R_4)]-\}_n-H$ (I) 10 by reacting in water a compound of formula (II) $CH_2=C(R_2)-C(=O)-N(R_3)(R_4)$ (II) with a chain limiting compound of formula (III) $Z-R_1-NH_2$; (b) isolating the telomer of formula (I) obtained at a stage (a); (c) reacting in water the telomer of formula (I) obtained at stage (b) with an acid chloride of formula (IV) $CH_2=C(R_5)-C(=O)-C_1$ at a molar ratio (IV)/(III) equal to or less than 10 and equal to or greater than 1 so that a macro monomer of formula (V) 20 $CH_2=C(R_5)-C(=O)NH-R_1-Z-\{CH_2-C(R_2)[C(=O)N(R_3)(R_4)]-\}_n-H$ (V) is obtained; (d) isolating the macro monomer of formula (V) obtained at stage (c); (e) copolymerizing in water the macro monomer of formula (V) isolated at stage (d) with a monomer selected from acrylamide, acrylic acid, acryloyl-aminoethanol or dimethyl-acrylamide and, if necessary, (f) purifying the thus obtained copolymer.

8 Claims, No Drawings

METHOD FOR PRODUCING WATER-SOLUBLE COMB-SHAPED COPOLYMERS

One subject of the present patent application is a novel method for preparing water-soluble graft copolymers.

International Application WO00/40958 describes a process for preparing acrylamide/poly(N-isopropyl-acrylamide) copolymers that include the following successive steps:

(a) synthesis of an N-isopropylacrylamide (NIPAM) telomer by radical polymerization;

(b) isolation of the telomer obtained, $(PNIPAM)_x NH_2$ by precipitation in ether, filtration then drying;

(c) reaction, in methylene chloride, of $(PNIPAM)_x\text{-}NH_2$ with a large excess of acrylic acid in the presence of cyclohexylcarbodiimide to lead to the poly(NIPAM) macromonomer bearing an acryl functional group at the chain end $(PNIPAM)_x$;

(d) isolation of the macromonomer obtained by precipitation in ether, filtration and then drying;

(e) copolymerization of the macromonomer obtained with acrylamide (AM) or dimethylacrylamide (DMA) in water, in order to obtain the copolymers grafted with $(PNIPAM)_x$, AM-g-$(PNIPAM)_x$ or DMA-g-$(PNIPAM)_x$ segments; and (f) purification by precipitation in water for DMA/$(PNIPAM)_x$ or in acetone for AM/$(PNIPAM)_x$, then ultrafiltration.

Within the scope of their research into attaining this type of graft polymer more easily, the Applicants applied themselves to developing a process for preparing these polymers, while limiting as much as possible the use of organic solvents.

This is why one subject of the invention is a process for preparing a comb copolymer of which the backbone is of the acrylamide, acrylic acid, acryloylaminoethanol or dimethylacrylamide type, grafted onto which are poly(N-alkylacrylamide) or poly(N,N-dialkylacrylamide) side segments, characterized in that it comprises the following successive steps:

(a) preparation of a poly(N-alkylacrylamide) or poly(N,N-dialkylacrylamide) telomer of formula (I):

in which n represents an integer greater than or equal to 2 and less than or equal to 100, Z represents a functional group capable of acting as a radical transfer agent, $R_1$ represents a divalent radical comprising from 1 to 4 carbon atoms, $R_2$ a hydrogen atom or a methyl group, $R_3$ a hydrogen atom or a linear or branched alkyl radical comprising from 1 to 4 carbon atoms and $R_4$, being identical to or different from $R_3$, represents a linear or branched alkyl radical comprising from 1 to 4 carbon atoms, by reaction in water of a compound of formula (II):

$$CH_2=C(R_2)-C(=O)-N(R_3)(R_4) \qquad (II)$$

in which $R_2$, $R_3$ and $R_4$ are as defined above, with a chain-limiting compound of formula (III):

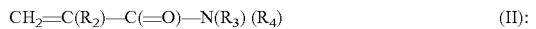

in which Z represents a functional group capable of acting as a radical transfer agent in a (II)/(III) molar ratio less than or equal to n and greater than or equal to n/10, in the presence of a polymerization initiator;

(b) isolation of the telomer of formula (I) obtained in step (a);

(c) reaction, in water, of the telomer of formula (I) obtained in step (b), with the acid chloride of formula (IV):

in which $R_5$ represents a hydrogen atom or a methyl radical, and in a (IV)/(III) molar ratio less than or equal to 10 and greater than or equal to 1 while keeping the pH of the reaction medium at a value between 6 and 13, preferably between 7 and 8, in order to obtain a macromonomer of formula (V):

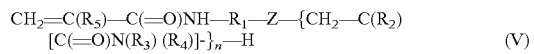

(d) isolation of the macromonomer of formula (V) obtained in step (c);

(e) copolymerization, in water, of the macromonomer of formula (V) isolated in step (d) with a monomer chosen from acrylamide, acrylic acid, acryloylaminoethanol or dimethylacrylamide; and if desired (f) purification of the copolymer obtained.

In the formulae (I), (II) and (V) as defined previously, when the radicals $R_3$ and $R_4$ represent a linear or branched alkyl radical comprising 1 to 4 carbon atoms, they are, in particular, methyl, ethyl, propyl, 1-methylethyl (isopropyl), butyl, 2-methylpropyl (isobutyl), 1-methylpropyl (sec-butyl) or 1,1-dimethylethyl (tert-butyl) radicals.

According to a first preferred aspect, in the formulae (I), (II) and (V), the radicals $R_3$ and $R_4$ each represent an isopropyl radical and therefore the subject of the process as defined above is preparing a comb copolymer of which the backbone is of the acrylamide, acrylic acid, acryloylaminoethanol or dimethylacrylamide type, grafted onto which are poly(N-isopropylacrylamide) side segments.

In the formulae (I), (III) and (V) as defined previously, $R_1$ more particularly represents a divalent alkanediyl radical such as, for example, a methylene, 1,2-ethanediyl, 1,3-propanediyl or 1,4-butanediyl radical.

According to a second preferred aspect, one subject of the process as defined previously is preparing a comb copolymer of which the backbone is of the acrylamide or dimethylacrylamide type, grafted onto which are poly(N-alkylacrylamide) or poly(N,N-dialkylacrylamide) side segments.

According to a first variant of the process as defined previously, carried out in place of the steps (b) and (c) are the following successive steps (b') and (c'):

(b') the pH of the reaction medium derived from step (a), without isolating the telomer of formula (I), is adjusted to a value between 6 and 13, and preferably between 7 and 8; and (c') added to the reaction medium derived from step (b') is the acid chloride of formula (IV) in a (IV)/(III) molar ratio less than or equal to 10 and greater than or equal to 1 while keeping the pH in the range indicated in step (b'), in order to obtain the macromonomer of formula (V).

According to this first variant as defined above, the steps (a) to (c') are preferably carried out in a single vessel.

According to a second variant of the process as defined previously, the monomer, chosen from acrylamide, acrylic acid, acryloylaminoethanol or dimethyl-acrylamide, is mixed with the reaction medium derived from step (c) without carrying out step (d).

According to this second variant of the process as defined above, the steps (a), (c) and (e) are carried out in a single vessel.

According to a last aspect of the present invention, one subject of this is a comb copolymer of which the backbone is of the acrylamide or dimethylacrylamide type, grafted onto which are poly(N,N-dialkylacrylamide) side segments, and more particularly a comb copolymer of which the backbone is of the acrylamide or dimethylacrylamide type, grafted onto which are poly(N,N-dimethylacrylamide) side segments.

The following examples illustrate the invention without however limiting it.

Example 1

Preparation of a Comb Copolymer Having a Backbone of the Acrylamide Type, Grafted onto which are poly(N-isopropylacrylamide) Side Segments, AM-g-NIPAM

(1) Preparation of a poly(N-isopropylacrylamide) Telomer

Poured into a thermostated reactor was an aqueous solution, concentrated to 1.77 mol per liter, of N-isopropylacrylamide (NIPAM), which was stirred under nitrogen sparging for around 1½ hours. Next, 2-aminoethanethiol hydrochloride (AET.HCl) was added in a given NIPAM/AET.HCl molar ratio varying from 30 to 75. After homogenizing for 5 minutes, a 17 wt % aqueous solution of ammonium persulfate was added at a flow rate of 0.35 g/min over around 30 minutes, then the reaction medium was left stirring under nitrogen sparging for a further 2 hours. At the end of the reaction, thin-layer chromatography was carried out on the medium (eluent: 6/4 (v/v) ethyl acetate/cyclohexane mixture) to check and record the absence of NIPAM.

Analysis of a sample of the reaction medium by high-performance liquid chromatography (HPLC) made it possible to determine the residual amount of NIPAM of around 1.5% indicating a degree of conversion greater than 92%.

The remainder of the sample was evaporated, dispersed in methanol, adjusted to neutral pH with methanolic potassium hydroxide, filtered and precipitated in ethyl ether. The telomer was recovered in solid form on which the alkalinity assay (potentiometric assay) was carried out. The reaction medium obtained comprised around 16.4% by weight of poly(N-isopropylacrylamide) telomer.

| Trial | NIPAM | AET•HCl | $(NH_4)_2S_2O_8$ | Remarks |
|---|---|---|---|---|
| 1(a) | 47.8 eq | 1 eq | 1% | Sudden 20° C. start, addition cloudy appearance |
| 1(b) | 47.8 eq | 1 eq | 1% | 30 min 20° C. start, addition white precipitate |
| 1(c) | 47.8 eq | 1 eq | 1% | 30 min 20° C. start, addition white precipitate |
| 1(d) | 47.8 eq | 1 eq | 1% | 30 min 5° C. start, clear addition |
| 1(e) | 30 eq | 1 eq | 1.6% | 30 min 5° C. start, clear addition |
| 1(f) | 75 eq | 1 eq | 0.67% | 30 min 5° C. start, clear addition |

The residual amount of NIPAM was, during all these trials, around 1.5% indicating a degree of conversion greater than 92%.

(2) Preparation of the macromonomer

Added to the reaction medium obtained in step (1) and comprising around 16.4 wt % of poly(N-isopropyl-acrylamide) telomer, was a normal aqueous solution of potassium hydroxide until a pH of around 8 was obtained. Next, acryloyl chloride (AcrCl) (molar equivalence determined with respect to the 2-aminoethanethiol introduced in the preceding step) was poured dropwise into the medium kept at a temperature of 10° C. and at a pH between 7 and 8 by addition of normal potassium hydroxide. After introduction of the acid chloride, the reaction medium was stirred for at least one hour while adjusting, if necessary, the pH.

At the end of the reaction, a sample of solution was removed for analysis by HPLC in order to measure the content of residual acrylic acid (AA). The remainder of the sample was evaporated and after re-dispersion in methanol it was precipitated in ethyl ether. The macromonomer was recovered in solid form and the alkalinity thereof was assayed (potentiometric assay). Several trials, recorded in the table below, were carried out:

| Trial | Telomer precursor | AcrCl | Residual AA measured by HPLC |
|---|---|---|---|
| 2(a) | 1(a); 1 eq | 2 eq | 0.13% |
| 2(b) | 1(b); 1 eq | 3 eq | 0.24% |
| 2(c) | 1(b); 1 eq | 5 eq | 0.49% |
| 2(d) | 1(c); 1 eq | 10 eq | 0.36% |
| 2(e) | 1(c); 1 eq | 1.1 eq | 0.05% |
| 2(f) | 1(d); 1 eq | 1.1 eq | 0.05% |
| 2(g) | 1(e); 1 eq | 2 eq | 0.18% |
| 2(h) | 1(f); 1 eq | 2 eq | / |

The equivalence ratios between the telomer and acryloyl chloride were calculated on the amount of AET.HCl introduced since no purification had taken place.

The degree of acylation was determined by assaying the alkalinity of the purified macromonomer. The same remark as previously may be made insofar as the extraction of the macromonomer proved difficult. Assaying of the residual acrylic acid resulting from the hydrolysis of the excess acryloyl chloride was also carried out.

(3) Synthesis of the Copolymer

Added to the reaction medium obtained in step 2 and into the reactor thermostated at 15° C. was a 50 wt % solution of acrylamide. (AM), then the whole mixture was diluted with deionized water to obtain a monomer concentration of around 10 wt % in given proportions. Nitrogen sparging was applied over two hours via the bottom of the reactor. The ammonium persulfate (0.18% by weight relative to the monomers) was added, followed by a solution of sodium metabisulfite (0.43% by weight relative to the monomers) over 30 minutes and the medium was left stirring for 4 h while keeping the temperature less than or equal to 30° C.

After precipitation in acetone, washing, filtration and drying, the desired copolymer was obtained.

Samples of 5% aqueous solution were prepared therefrom in order to evaluate the heat-thickening properties. Several trials, recorded in the table below, were carried out:

| Trial | Macromonomer precursor | AM | $(NH_4)_2S_2O_8$ | $Na_2S_2O_5$ |
|---|---|---|---|---|
| 3(a) | 2(a); 12.5 wt % | 87.5 wt % | 645 ppm | 210 ppm over 30 min |
| 3(b) | 2(b); 12.5 wt % | 87.5 wt % | 645 ppm | 210 ppm over 30 min |
| 3(c) | 2(c); 12.5 wt % | 87.5 wt % | 645 ppm | 210 ppm over 30 min |
| 3(d) | 2(d); 12.5 wt % | 87.5 wt % | 645 ppm | 210 ppm over 30 min |
| 3(e) | 2(e); 12.5 wt % | 87.5 wt % | 645 ppm | 210 ppm over 30 min |
| 3(f) | 2(f); 22.2 wt % | 77.8 wt % | 645 ppm | 210 ppm over 30 min |
| 3(g) | 2(g); 12.5 wt % | 87.5 wt % | 645 ppm | 210 ppm over 30 min |
| 3(h) | 2(h); 12.5 wt % | 87.5 wt % | 645 ppm | 210 ppm over 30 min |

In these trials, the degree of residual acrylamide approached 1000 ppm.

Example 2

Preparation of a Comb Copolymer Having an Acrylamide Type Backbone, Grafted onto which are poly(N,N-dimethylacrylamide) Side Segments

(1) Preparation of a poly(N,N-dimethylacrylamide) Telomer

This telomer was obtained according to the method described in step (1) of example 1 starting from N,N-dimethylacrylamide (DMAM) and their particular data recorded in the following table:

| Trial | DMAM/AET•HCl molar ratio | $(NH_4)_2S_2O_8$ | |
|---|---|---|---|
| 4(a) | 300/1 | 1% | Added over 30 minutes |
| 4(b) | 300/1 | 1% | Added over 30 minutes |
| 4(c) | 75/1 | 1% | Added over 30 minutes |
| 4(d) | 75/1 | 1% | Sudden addition |
| 4(e) | 300/1 | 1% | |

At the end of the polymerization, a telomer in solution in water at a concentration of 16.2% was obtained.

(2) Preparation of the Macromonomer

This macromonomer was obtained according to the method described in step (2) of example 1 from the aqueous solution of poly(N,N-dimethylacrylamide) telomer obtained in step (1); a 15.6 wt % aqueous solution of macromonomer was obtained.

At the end of the reaction, a sample of solution was removed for analysis by HPLC to measure the content of residual acrylic acid (AA). The remainder of the sample was evaporated, and after re-dispersion in methanol, it was precipitated in ether. The macromonomer was recovered in solid form and the alkalinity thereof was assayed (potentiometric assay). Several trials, recorded in the table below, were carried out:

| Trial | Telomer precursor | AcrCl |
|---|---|---|
| 5(a) | 4(a); 1 eq | 2 eq |
| 5(b) | 4(b); 1 eq | 2 eq |
| 5(c) | 4(c); 1 eq | 2 eq |
| 5(d) | 4(d); 1 eq | 2 eq |
| 5(e) | 4(e); 1 eq | 2 eq |

(3) Synthesis of the Copolymer

Starting from aqueous solutions of DMAM macromonomers obtained in the preceding step (2) and not purified, several copolymers were synthesized. The trials are recorded in the table below:

| Trial | Initial macro-monomer | AM/macro-monomer weight ratio | 1 - Initiation; 2 - Transfer agent; 3 - pH of the medium |
|---|---|---|---|
| 6(a) | 5(e) | 77/11 | 1 - $(NH_4)_2S_2O_8$ 500 ppm + $Na_2S_2O_5$ 500 ppm (flow rate 4.6 ppm/min); 2 - 0% 3 - pH = 6.65 |
| 6(b) | 5(e) | 77/11 | 1 - $(NH_4)_2S_2O_8$ 500 ppm + TEMED* 1000 ppm; 2 - 0%; 3 - pH = 6.5 |
| 6(c) | 5(e) | 77/11 | 1 - $(NH_4)_2S_2O_8$ 1000 ppm + TEMED 5000 ppm; 2 - 0%; 3 - pH = 6.65 |
| 6(d) | 5(a) | 92/8 | 1 - $(NH_4)_2S_2O_8$ 500 ppm + $Na_2S_2O_5$ 500 ppm; 2 - 0% |
| 6(e) | 5(b) | 92/8 | 1 - $(NH_4)_2S_2O_8$ 500 ppm + $Na_2S_2O_5$ 500 ppm; 2 - 0% |
| 6(f) | 5(b) | 92/8 | 1 - $(NH_4)_2S_2O_8$ 1000 ppm at 75° C.; 2 - 0% |
| 6(g) | 5(b) | 92/8 | 1 - $(NH_4)_2S_2O_8$ 1000 ppm at 75° C.; 2 - $NaH_2PO_2$ 50 ppm |
| 6(h) | 5(b) | 92/8 | 1 - $(NH_4)_2S_2O_8$ 1000 ppm at 75° C.; 2 - $NaH_2PO_2$ 2000 ppm |
| 6(i) | 5(b) | 92/8 | 1 - $(NH_4)_2S_2O_8$ 1000 ppm at 75° C.; 2 - $NaH_2PO_2$ 1000 ppm |
| 6(j) | 5(b) | 92/8 | 1 - $(NH_4)_2S_2O_8$ 1000 ppm at 75° C.; 2 - $NaH_2PO_2$ 250 ppm |
| 6(k) | 5(c) | 92/8 | 1 - $(NH_4)_2S_2O_8$ 500 ppm + $Na_2S_2O_5$ 500 ppm; 2 - 0% |
| 6(l) | 5(d) | 92/8 | 1 - $(NH_4)_2S_2O_8$ 500 ppm + $Na_2S_2O_5$ 500 ppm; 2 - 0% |
| 6(m) | 5(c) | 87.5/12.5 | 1 - $(NH_4)_2S_2O_8$ 500 ppm + $Na_2S_2O_5$ 500 ppm; 2 - 0% |
| 6(n) | 5(d) | 87.5/12.5 | 1 - $(NH_4)_2S_2O_8$ 500 ppm + $Na_2S_2O_5$ 500 ppm; 2 - 0% |

*TEMED: tetramethylethylenediamine

Viscosities of 3 wt % aqueous solutions of comb polymers.

| Polymers | Viscosity Brookfield viscometer Speed: 5 rpm; spindle M5 or M6 depending on the expected values |
|---|---|
| 6(d) | 9500 mPa·s |
| 6(e) | Very high |
| 6(f) | Very high |
| 6(g) | Very high |
| 6(h) | 80 mPa·s |
| 6(i) | 120 mPa·s |
| 6(j) | 400 mPa·s |
| 6(k) | 760 mPa·s |
| 6(l) | 7500 mPa·s |
| 6(m) | 290 mPa·s |
| 6(n) | 400 mPa·s |

The invention claimed is:

1. A process for preparing a comb copolymer of which the backbone is of the acrylamide, acrylic acid, acryloylaminoethanol or dimethylacrylamide type, grafted onto which are poly(N-alkylacrylamide) or poly(N,N-dialkylacrylamide) side segments, characterized in that it comprises the following successive steps:

(a) preparation of a poly(N-alkylacrylamide) or poly(N,N-dialkylacrylamide) telomer of formula (I):

in which n represents an integer greater than or equal to 2 and less than or equal to 100, Z represents a functional group capable of acting as a radical transfer agent, $R_1$ represents a divalent radical comprising from 1 to 4 carbon atoms, $R_2$ a hydrogen atom or a methyl group, $R_3$ a hydrogen atom or a linear or branched alkyl radical comprising from 1 to 4 carbon atoms and $R_4$, being identical to or different from $R_3$, represents a linear or branched alkyl radical comprising from 1 to 4 carbon atoms, by reaction in water of a compound of formula (II):

$$CH_2=C(R_2)-C(=O)-N(R_3)(R_4) \quad (II)$$

in which $R_2$, $R_3$ and $R_4$ are as defined above, with a chain-limiting compound of formula (III):

$$Z-R_1-NH_2 \quad (III)$$

in which Z represents a functional group capable of acting as a radical transfer agent in a (II)/(III) molar ratio less than or equal to n and greater than or equal to n/10, in the presence of a polymerization initiator;
- (b) isolation of the telomer of formula (I) obtained in step (a);
- (c) reaction, in water, of the telomer of formula (I) obtained in step (b), with the acid chloride of formula (IV):

$$CH_2=C(R_5)-C(=O)-Cl \quad (IV)$$

in which $R_5$ represents a hydrogen atom or a methyl radical, and in a (IV)/(III) molar ratio less than or equal to 10 and greater than or equal to 1 while keeping the pH of the reaction medium at a value between 6 and 13, preferably between 7 and 8, in order to obtain a macromonomer of formula (V):

$$CH_2=C(R_5)-C(=O)NH-R_1-Z-\{CH_2-C(R_2)[C(=O)N(R_3)(R_4)]-\}_n-H \quad (V)$$

- (d) isolation of the macromonomer of formula (V) obtained in step (c);
- (e) copolymerization, in water, of the macromonomer of formula (V) isolated in step (d) with a monomer chosen from acrylamide, acrylic acid, acryloylaminoethanol or dimethylacrylamide; and if desired
- (f) purification of the copolymer obtained.

2. The process as defined in claim 1, for preparing a comb copolymer of which the backbone is of the acrylamide, acrylic acid, acryloylaminoethanol or dimethylacrylamide type, grafted onto which are poly(N-isopropylacrylamide) side segments.

3. The process as defined in claim 1, for preparing a comb copolymer of which the backbone is of the acrylamide or dimethylacrylamide type, grafted onto which are poly(N-alkylacrylamide) or poly(N,N-dialkylacrylamide) side segments.

4. A variant of the process as defined in claim 1, in which:
- (b') the pH of the reaction medium derived from step (a), without isolating the telomer of formula (I), is adjusted to a value between 6 and 13, and preferably between 7 and 8; and
- (c') added to the reaction medium derived from step (b') is the acid chloride of formula (IV) in a (IV)/(III) molar ratio less than or equal to 10 and greater than or equal to 1 while keeping the pH in the range indicated in step (b'), in order to obtain the macromonomer of formula (V).

5. The variant of the process as defined in claim 4, in which the steps (a) to (c') are carried out in a single vessel.

6. A variant of the process as defined in claim 1, according to which the monomer, chosen from acrylamide, acrylic acid, acryloylaminoethanol or dimethylacrylamide, is mixed with the reaction medium derived from step (c) without carrying out step (d).

7. The variant as defined in claim 6, in which the steps (a), (c) and (e) are carried out in a single vessel.

8. The process as defined in claim 2, for preparing a comb copolymer of which the backbone is of the acrylamide or dimethylacrylamide type, grafted onto which are poly(N-alkylacrylamide) or poly(N,N-dialkylacrylamide) side segments.

* * * * *